United States Patent
Cole et al.

(10) Patent No.: US 7,842,715 B2
(45) Date of Patent: Nov. 30, 2010

(54) N-BENZOYL- AND N-BENZYLPYRROLIDIN-3-YLAMINES AS HISTAMINE-3 ANTAGONISTS

(75) Inventors: Derek Cecil Cole, New City, NY (US); Magda Asselin, Mahwah, NJ (US); Joseph Raymond Stock, Monroe, NY (US); Jin-In Kim, Princeton, NJ (US)

(73) Assignee: Wyeth LLC, Madison, NJ (US)

( * ) Notice: Subject to any disclaimer, the term of this patent is extended or adjusted under 35 U.S.C. 154(b) by 646 days.

(21) Appl. No.: 11/804,686

(22) Filed: May 18, 2007

(65) Prior Publication Data
US 2007/0270440 A1    Nov. 22, 2007

Related U.S. Application Data

(60) Provisional application No. 60/801,905, filed on May 19, 2006.

(51) Int. Cl.
*A61K 31/4025* (2006.01)
*C07D 207/04* (2006.01)

(52) U.S. Cl. ........................ 514/422; 548/517; 548/518; 514/408

(58) Field of Classification Search ................. 548/517, 548/518; 514/408, 422
See application file for complete search history.

(56) References Cited

U.S. PATENT DOCUMENTS

| | | | |
|---|---|---|---|
| 3,933,829 A | 1/1976 | Archibald et al. | |
| 4,159,331 A | 6/1979 | McCall | |
| 4,166,853 A | 9/1979 | McCall | |
| 5,747,485 A * | 5/1998 | Doherty et al. | 514/210.02 |
| 5,883,096 A | 3/1999 | Lowe et al. | |
| 6,451,842 B1 * | 9/2002 | Shiota et al. | 514/422 |
| 6,541,499 B1 | 4/2003 | Bastian et al. | |
| 2004/0102360 A1 | 5/2004 | Barnett et al. | |
| 2004/0186148 A1 | 9/2004 | Shankar et al. | |
| 2005/0256102 A1 | 11/2005 | Claiborne et al. | |
| 2006/0014733 A1 | 1/2006 | Howard, Jr. et al. | |
| 2006/0089496 A1 | 4/2006 | Lam et al. | |
| 2006/0166960 A1 | 7/2006 | Aslanian et al. | |
| 2007/0032475 A1 | 2/2007 | Ye et al. | |

FOREIGN PATENT DOCUMENTS

| | | |
|---|---|---|
| DE | 2311570 | 9/1973 |
| EP | 0236140 A2 | 9/1987 |
| EP | 1847532 A1 | 10/2007 |
| WO | WO 94/22826 | 10/1994 |
| WO | WO 97/24324 A1 | 7/1997 |
| WO | WO 98/48800 | 11/1998 |
| WO | WO 99/09984 A1 | 3/1999 |
| WO | WO 00/05225 A1 | 2/2000 |
| WO | WO 00/35435 A1 | 6/2000 |
| WO | WO 01/42224 A1 | 6/2001 |
| WO | WO 01/74773 A2 | 10/2001 |
| WO | WO 02/055496 A1 | 7/2002 |
| WO | WO 03/004467 A2 | 1/2003 |
| WO | WO 03/018576 A1 | 3/2003 |
| WO | WO 03/040402 A2 | 5/2003 |
| WO | WO 03/082272 A1 | 10/2003 |
| WO | WO 03/086279 A1 | 10/2003 |
| WO | WO 2004/052858 A2 | 6/2004 |
| WO | WO 2004/081011 A1 | 9/2004 |
| WO | WO 2005/000309 A2 | 1/2005 |
| WO | WO 2005/115977 A1 | 12/2005 |
| WO | WO 2006/011042 A1 | 2/2006 |
| WO | WO 2006/019833 A1 | 2/2006 |
| WO | WO 2006/023462 A1 | 3/2006 |
| WO | WO 2006/040281 A1 | 4/2006 |
| WO | WO 2007/107539 A1 | 9/2007 |
| WO | WO 2007/108936 A | 9/2007 |
| WO | WO 2007/115933 A1 | 10/2007 |
| WO | WO 2008/045371 A | 4/2008 |

OTHER PUBLICATIONS

Koh et al. "Conformational and structural features determining in vitro antimalarial activity in some indolo 3, 2-couinolines, anilinoquinolines and tetrahydroindolo3, 2-dbenzazepines". European Journal of Medicinal Chemistry. vol. 29, No. 2, 1994, p. 107-113.

Blandina, P. et al., "Inhibition of cortical acetylcholine release and cognitive performance by histamine H3 receptor activation in rats", Br J Pharmacol. Dec. 1996;119(8):1656-64.

Database Chemcats [Online] chemical abstract service. Ambinter Stock Screening Collection; Feb. 13, 2008.

Esbenshade et al., "Histamine H3 receptor antagonists: preclinical promise for treating obesity and cognitive disorders". Mol Interv. Apr. 2006;6(2):77-88.

(Continued)

*Primary Examiner*—Golam M Shameem
(74) *Attorney, Agent, or Firm*—Jennifer A. Kispert; Robert T. Ronau

(57) ABSTRACT

The present invention provides a compound of formula I and the use thereof for the treatment of a central nervous system disorder related to or affected by the histamine-3 receptor.

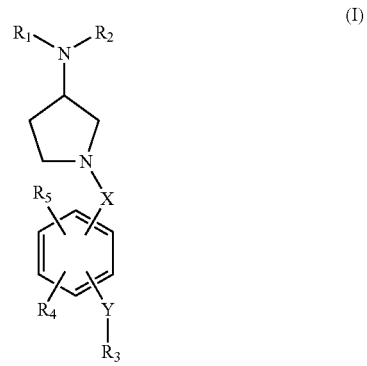

14 Claims, No Drawings

OTHER PUBLICATIONS

Fox, G. B. et al., "Effects of histamine H(3) receptor ligands GT-2331 and ciproxifan in a repeated acquisition avoidance response in the spontaneously hypertensive rat pup", Behav Brain Res. Apr. 1, 2002;131(1-2):151-61.

Hancock et al., Perspectives on cognitive domains. H3 receptor ligands and neurological disease. Expert Opin Investig Drugs. Oct. 2004;13(10):1237-48.

Komater, V.A., et al., "H3 receptor blockade by thioperamide enhances cognition in rats without inducing locomotor sensitization", Psychopharmacology (Berl). Jun. 2003;167(4):363-72.

Meguro, K. et al., "Effects of thioperamide, a histamine H3 antagonist, on the step-through passive avoidance response and histidine decarboxylase activity in senescence-accelerated mice", Pharmacol Biochem Behav. Mar. 1995;50(3):321-5.

Miyazaki, S. et al., "Effects of clobenpropit (VUF-9153), a histamine H3-receptor antagonist, on learning and memory, and on cholinergic and monoaminergic systems in mice", Life Sci. 1997;61(4):355-61.

PCT International Search Report, for corresponding PCT/US2007/011765, International filing date May 16, 2007.

Prast, H. et al., "Histaminergic neurons facilitate social memory in rats", Brain Res. Sep. 23, 1996;734(1-2):316-8.

* cited by examiner

N-BENZOYL- AND N-BENZYLPYRROLIDIN-3-YLAMINES AS HISTAMINE-3 ANTAGONISTS

This application claims the benefit under 35 U.S.C. §119(e) to U.S. provisional application No. 60/801,905, filed May 19, 2006, which is hereby incorporated by reference in its entirety.

BACKGROUND OF THE INVENTION

The histamine-3 (H3) receptor is one of four histamine receptor subtypes (H1-H4), all of which are members of the larger G-protein-coupled receptor (GCPR) superfamily of receptors. The H3 receptor is predominantly expressed in the central nervous system. In the brain, it is located in regions associated with learning and memory such as the cerebral cortex, hippocampus and striatum. The H3 receptor acts as both auto- and hetero-receptor to regulate the release of histamine and other neurotransmitters. Within the cortex, the H3 receptor appears to directly modify GABA release from cortical interneurons. Antagonism of the H3 receptor produces a decrease in GABA release and disinhibition of the cortical cholinergic system, resulting in increased acetylcholine levels (Bacciottini, L. et al, Behavioral Brain Research, 124, 2001, 183-194). In addition to direct regulation of cholinergic neurotransmission, the H3 receptor has been shown to modulate the release of dopamine, serotonin and norepinephrine (Leurs, R., et al., Trends in Pharmacological Sciences, 19, 1998, 177-183). A postmortem study in humans suggests that a decrease in brain histamine levels may contribute to the cognitive decline which occurs in Alzheimer's disease, directly or through the cholinergic system (Panula, P., et al., Neuroscience, 82, 1998, 993-997). H3 agonists have been reported to impair memory in various tasks, such as object recognition, passive avoidance (Blandina, P., et al., British Journal of Pharmacology, 119(8), 1996, 1656-1664) and social olfactory memory (Prast, H., et al., 734, 1996, 316-318), whereas H3 antagonists have been reported to rescue impairments produced pharmacologically or genetically, i.e. Miyazaki, S., et al., Life Sciences, 61, 1997, 355-361; Meguro, K., et al., Pharmacology, Biochemistry and Behavior, 50, 1995, 321-325; Fox, G. B., et. al, Behavioral Brain Research, 131, 2002, 151-161; and Komater, V. A., et al., Psychopharmacology, 167, 2003, 363-372.

Accumulating neuroanatomical, neurochemical, pharmacological and behavioral data support the concept that H3 receptor antagonists may improve cognitive performance in disease states such as mild cognitive impairment and Alzheimer's disease and may have therapeutic value in the treatment of attention deficit hyperactivity disorder (ADHD), schizophrenia, obesity and sleep disorders.

Therefore, it is an object of this invention to provide compounds which are inhibitors of the H3 receptor and are useful as therapeutic agents in the treatment of a variety of central nervous system disorders related to or affected by the H3 receptor.

It is another object of this invention to provide therapeutic methods and pharmaceutical compositions useful for the treatment of central nervous system disorders related to or affected by the H3 receptor.

It is a feature of this invention that the compounds provided may also be useful to further study and elucidate the H3 receptor.

SUMMARY OF THE INVENTION

The present invention provides an N-benzoyl- or N-benzylpyrrolidin-3-ylamine compound of formula I

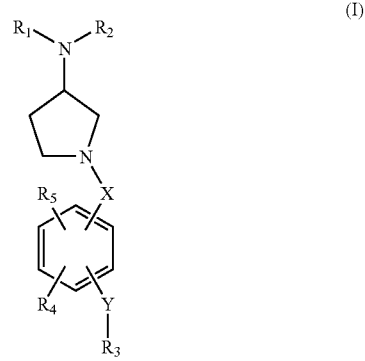

wherein
  X is CO, $CH_2$ or $SO_m$;
  Y is $NR_6$, $NR_6CO$, O or $SO_p$;
  m and p are each individually 0 or an integer of 1 or 2;
  $R_1$ and $R_2$ are each independently H or an optionally substituted alkyl group or $R_1$ and $R_2$ may be taken together with the atom to which they are attached to form an optionally substituted 4- to 7-membered ring optionally containing one or two additional heteroatoms selected from N, O or S
  $R_3$ is $NR_7R_8$ or an aryl or heteroaryl group each group optionally substituted with the proviso that when Y is $NR_6$, O or $SO_p$ then $R_3$ must be an aryl or heteroaryl group each group optionally substituted;
  $R_4$ and $R_5$ are each independently H, halogen, $OR_9$ or an alkyl, alkenyl, alkynyl, cycloalkyl, cycloheteroalkyl, aryl or heteroaryl group each optionally substituted;
  $R_6$ and $R_9$ are each independently H or an optionally substituted alkyl group; and
  $R_7$ and $R_8$ are taken together with the atom to which they are attached to form an optionally substituted fused bicyclic or tricyclic 9- to 13-membered ring system optionally containing one to three additional heteroatoms selected from N, O or S; or a stereoisomer thereof or a pharmaceutically acceptable salt thereof.

The present invention also provides methods and compositions useful for the therapeutic treatment of central nervous system disorders related to or affected by the Histamine-3 receptor.

DETAILED DESCRIPTION OF THE INVENTION

Alzheimer's disease (AD) is characterized by a progressive loss of memory and cognitive function and is the most common cause of dementia in the elderly. AD is believed to affect approximately 15-20 million people worldwide. The goal of treatment in AD, in addition to reversing the disease process, is to improve or at least slow the loss of memory and cognition and to maintain independent function in patients with mild to moderate disease. AD is characterized by numerous deficits in neurotransmitter function (Möller, H-J., European Neuropsychopharmacology, 9, 1999, S53-S59), further a postmortem study in humans suggests that a decrease in brain histamine levels may contribute to the cognitive decline associated with AD, directly or through the cholinergic system (Panula, P., et al., Neuroscience, 82, 1998, 993-997). Histamine-3 (H3) receptor antagonists have been reported to rescue impairments produced pharmacologically or genetically (Miyazaki, S., et al., Life Sciences, 61, 1997, 355-361; Meguro, K., et al., Pharmacology, Biochemistry and Behavior, 50, 1995, 321-325; Fox, G. B., et. al, Behavioral Brain Research, 131, 2002, 151-161; and Komater, V. A., et al., Psychopharmacology, 167, 2003, 363-372). Neuroanatomical, neurochemical, pharmacological and behavioral data support the belief that H3 receptor antagonists may improve cognitive performance in disease states such as mild cognitive impairment and Alzheimer's disease and may have therapeutic value in the treatment of attention deficit hyperactivity disorder (ADHD), schizophrenia, obesity and sleep disorders. To that end, compounds which inhibit the H3 receptor and act as H3 antagonists are earnestly sought.

Surprisingly it has now been found that N-benzoyl- and N-benzylpyrrolidin-3-ylamine compounds of formula I demonstrate H-3 affinity along with significant sub-type selectivity and function as H-3 antagonists. Advantageously, said formula I compounds are effective therapeutic agents for the treatment of central nervous system (CNS) disorders associated with or affected by the H-3 receptor. Accordingly, the present invention provides an N-benzoyl- or N-benzylpyrrolidin-3-ylamine compound of formula I

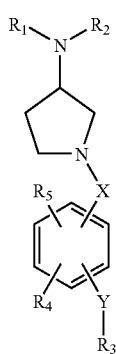

(I)

wherein
X is CO, $CH_2$ or $SO_m$;
Y is $NR_6$, $NR_6CO$, O or $SO_p$;
m and p are each individually 0 or an integer of 1 or 2;
$R_1$ and $R_2$ are each independently H or an optionally substituted alkyl group or $R_1$ and $R_2$ may be taken together with the atom to which they are attached to form an optionally substituted 4- to 7-membered ring optionally containing one or two additional heteroatoms selected from N, O or S
$R_3$ is $NR_7R_8$ or an aryl or heteroaryl group each group optionally substituted with the proviso that when Y is $NR_6$, O or $SO_p$ then $R_3$ must be an aryl or heteroaryl group each group optionally substituted;
$R_4$ and $R_5$ are each independently H, halogen, $OR_9$ or an alkyl, alkenyl, alkynyl, cycloalkyl, cycloheteroalkyl, aryl or heteroaryl group each optionally substituted;
$R_6$ and $R_9$ are each independently H or an optionally substituted alkyl group; and $R_7$ and $R_8$ are taken together with the atom to which they are attached to form an optionally substituted fused bicyclic or tricyclic 9- to 13-membered ring system optionally containing one to three additional heteroatoms selected from N, O or S; or a stereoisomer thereof or a pharmaceutically acceptable salt thereof.

It is understood that the claims encompass all possible stereoisomers and prodrugs. Moreover, unless stated otherwise, each alkyl, alkenyl, alkynyl, cycloalkyl cycloheteroalkyl, aryl or heteroaryl group is contemplated as being optionally substituted.

An optionally substituted moiety may be substituted with one or more substituents. The substituent groups, which are optionally present, may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl or lower alkoxy groups. Unless otherwise specified, typically, 0-4 substituents may be present. When any of the foregoing substituents represents or contains an alkyl substituent group, this may be linear or branched and may contain up to 12 carbon atoms, preferably up to 6 carbon atoms, more preferably up to 4 carbon atoms.

As used herein, the term alkyl includes both $(C_1-C_{10})$ straight chain and $(C_3-C_{12})$ branched-chain (unless defined otherwise) monovalent saturated hydrocarbon moiety. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, and the like. Specifically included within the definition of alkyl are those alkyl groups that are optionally substituted. Suitable alkyl substitutions include, but are not limited to, CN, OH, $NR_{10}$, $R_{11}$, halogen, phenyl, carbamoyl, carbonyl, alkoxy or aryloxy.

As used herein, the term haloalkyl designates a $C_nH_{2n+1}$ group having from one to 2n+1 halogen atoms which may be the same or different. Examples of haloalkyl groups include $CF_3$, $CH_2Cl$, $C_2H_3BrCl$, $C_3H_5F_2$, or the like.

The term halogen, as used herein, designates fluorine, chlorine, bromine, and iodine.

The term alkenyl, as used herein, refers to either a $(C_2-C_{10})$ straight chain or $(C_3-C_{10})$ branched-chain monovalent hydrocarbon moiety containing at least one double bond. Such hydrocarbon alkenyl moieties may be mono or polyunsaturated, and may exist in the E or Z configurations. The compounds of this invention are meant to include all possible E and Z configurations. Examples of mono or polyunsaturated hydrocarbon alkenyl moieties include, but are not limited to, chemical groups such as vinyl, 2-propenyl, isopropenyl, crotyl, 2-isopentenyl, butadienyl, 2-(butadienyl), 2,4-pentadienyl, 3-(1,4-pentadienyl), and higher homologs, isomers, or the like.

The term alkynyl, as used in the specification and claims, designates either a $(C_2-C_{10})$ straight chain or $(C_3-C_{10})$ branched chain monovalent hydrocarbon moiety having at least one triple bond. Such hydrocarbon alkynyl moieties may be mono or polyunsaturated, and may exist in the E or Z configurations. The compounds of this invention are meant to include all possible E and Z configurations. Examples of mono or polyunsaturated hydrocarbon alkynyl moieties include, but are not limited to, propynyl, butynyl, 1,3-butadiynyl, pentynyl, hexynyl, or the like.

The term cycloalkyl, as used herein, refers to a monocyclic, bicyclic, tricyclic, fused, bridged, or spiro monovalent saturated hydrocarbon moiety of 3-10 carbon atoms. Examples of cycloalkyl moieties include, but are not limited to, chemical groups such as cyclopropyl, cyclobutyl, cyclopentyl, cyclohexyl, cycloheptyl, norbornyl, adamantyl, spiro[4,5]decanyl, or the like.

The term cycloheteroalkyl, as used herein, designates a $C_5$-$C_7$cycloalkyl ring system containing 1, 2 or 3 heteroatoms, which may be the same or different, selected from N, O or S and optionally containing one double bond. Exemplary of the cycloheteroalkyl ring systems included in the term as designated herein are the following rings wherein $X_1$ is NR', O or S and R' is H or an optional substituent as defined hereinabove.

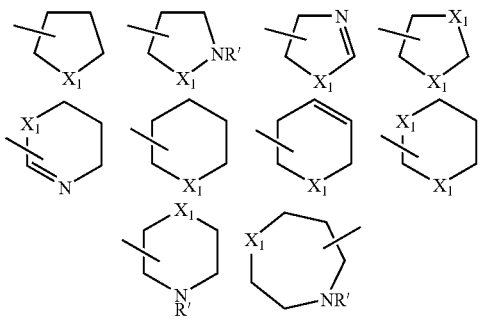

The term aryl, as used herein, refers to an aromatic carbocyclic moiety of up to 20 carbon atoms, which may be a single ring (monocyclic) or multiple rings (bicyclic, up to three rings) fused together or linked covalently. Examples of aryl moieties include, but are not limited to, chemical groups such as phenyl, 1-naphthyl, 2-naphthyl, biphenyl, anthryl, phenanthryl, fluorenyl, acenaphthenyl, or the like.

The term heteroaryl as used herein designates an aromatic heterocyclic ring system, which may be a single ring (monocyclic) or multiple rings (bicyclic, up to three rings) fused together or linked covalently. Preferably, heteroaryl is a 5- to 6-membered monocyclic ring or a 9- to 13-membered bicyclic ring system. The rings may contain from one to four hetero atoms selected from nitrogen, oxygen, or sulfur, wherein the nitrogen or sulfur atoms are optionally oxidized, or the nitrogen atom is optionally quarternized. Examples of heteroaryl moieties include, but are not limited to, heterocycles such as furan, thiophene, pyrrole, pyrazole, imidazole, oxazole, isoxazole, thiazole, isothiazole, oxadiazole, triazole, pyridine, pyrimidine, pyrazine, pyridazine, benzimidazole, benzoxazole, benzisoxazole, benzothiazole, benzofuran, benzothiophene, thienylpyrimidinyl, thianthrene, dibenzofuran, dibenzothiophene, indole, indazole, quinoline, isoquinoline, quinazoline, quinoxaline, purine, or the like.

Exemplary of the fused bicyclic or tricyclic 9- to 13-membered ring system formed when $R_7$ and $R_8$ are taken together with the nitrogen atom to which they are attached are indolyl, indazolyl, benzimidazolyl, tetrahydrocarbazolyl, hexahydroindolizinoindolonyl, tetrahydropyranoindolyl, azaindolyl, imidazopyridinyl, indolinyl, tetrahydroquinolinlyl, pyridoindolyl, dihydrodibenzoazepinyl, or the like.

In the specification and claims, when $R_3$ represents heteroaryl, the heteroaryl group is attached to Y though a carbon atom in the heteroaryl ring system.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}C$— or $^{14}C$-enriched carbon are within the scope of this invention.

The compounds of the present invention may be converted to salts, in particular pharmaceutically acceptable salts using art recognized procedures. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethyl-propylamine, or a mono-, di-, or trihydroxy lower alkylamine, for example mono-, di- or triethanolamine. Internal salts may furthermore be formed. Salts which are unsuitable for pharmaceutical uses but which can be employed, for example, for the isolation or purification of free compounds or their pharmaceutically acceptable salts, are also included. The term "pharmaceutically acceptable salt", as used herein, refers to salts derived from organic and inorganic acids such as, for example, acetic, propionic, lacetic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

Compounds of the invention include esters, carbamates or other conventional prodrug forms, which in general, are functional derivatives of the compounds of the invention and which are readily converted to the inventive active moiety in vivo.

Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Preferred compounds of the invention are those compounds of formula I wherein X is CO or $CH_2$. Another group of preferred compounds is those formula I compounds wherein Y is $NR_6$, $NR_6CO$ or O. Also preferred are those formula I compounds wherein $R_1$ and $R_2$ are taken together with the atom to which they are attached to form an optionally substituted 5-membered ring.

More preferred compounds of the invention are those compounds of formula I wherein X is CO or $CH_2$ and $R_1$ and $R_2$ are taken together with the atom to which they are attached to form a 5-membered ring. Another group of more preferred compounds is those compounds of formula I wherein X is CO or CH₂ and Y is O. A further group of more preferred compounds are those compounds of formula I wherein X is CO; Y is O; and R₁ and R₂ are taken together with the atom to which they are attached to form a 5-membered ring.

Among the preferred compounds of the invention are:
(3'S)-1'-(4-phenoxybenzoyl)-1,3'-bipyrrolidine;
N-(4-{[3-(dimethylamino)pyrrolidin-1-yl]carbonyl}phenyl)-1-naphthamide;
N-(4-{[3-(dimethylamino)pyrrolidin-1-yl]carbonyl}phenyl)quinoline-2-carboxamide;
N-(4-{[3-(dimethylamino)pyrrolidin-1-yl]carbonyl}phenyl)-1-benzothiophene-2-carboxamide;
N-(4-{[3-(dimethylamino)pyrrolidin-1-yl]carbonyl}phenyl)-2-phenylquinazolin-4-amine;
N-(4-{[3-(dimethylamino)pyrrolidin-1-yl]carbonyl}phenyl)-9H-purin-6-amine;
N-(4-{[3-(dimethylamino)pyrrolidin-1-yl]carbonyl}phenyl)pyridin-2-amine;
N-(4-{[3-(dimethylamino)pyrrolidin-1-yl]carbonyl}phenyl)thieno[3,2-d]pyrimidin-4-amine;
N-(4-{[3-(dimethylamino)pyrrolidin-1-yl]carbonyl}phenyl)-7-methylthieno[3,2-d]pyrimidin-4-amine;
N-(4-{[3-(dimethylamino)pyrrolidin-1-yl]carbonyl}phenyl)isoquinolin-1-amine;
N-(4-{[3-(dimethylamino)pyrrolidin-1-yl]carbonyl}phenyl)-5-(trifluoromethyl)pyridin-2-amine;
N-(4-{[3-(dimethylamino)pyrrolidin-1-yl]carbonyl}phenyl)pyrimidin-2-amine;
1-[4-(1-benzothien-3-ylamino)benzoyl]-N,N-dimethylpyrrolidin-3-amine;
N-(4-{[3-(dimethylamino)pyrrolidin-1-yl]carbonyl}phenyl)-2,1,3-benzothiadiazol-4-amine;
N-(4-{[3-(dimethylamino)pyrrolidin-1-yl]carbonyl}phenyl)-1H-indol-5-amine;
3-chloro-N-(4-{[3-(dimethylamino)pyrrolidin-1-yl]carbonyl}phenyl)thiophene-2-carboxamide;
N-(4-{[3-(dimethylamino)pyrrolidin-1-yl]carbonyl}phenyl)-2-naphthamide;
N-(4-{[3-(dimethylamino)pyrrolidin-1-yl]carbonyl}phenyl)isoquinoline-1-carboxamide;
N-(4-{[3-(dimethylamino)pyrrolidin-1-yl]carbonyl}phenyl)-1-methyl-1H-indole-2-carboxamide;
N-(4-{[3-(dimethylamino)pyrrolidin-1-yl]carbonyl}phenyl)-1,2,3,4-tetrahydronaphthalene-2-carboxamide;
N-(4-{[3-(dimethylamino)pyrrolidin-1-yl]carbonyl}phenyl)-5-methyl-3-phenylisoxazole-4-carboxamide;
N-(4-{[3-(dimethylamino)pyrrolidin-1-yl]carbonyl}phenyl)-4-methoxyquinoline-2-carboxamide;
N-(4-{[3-(dimethylamino)pyrrolidin-1-yl]carbonyl}phenyl)-7-methoxy-1-benzofuran-2-carboxamide;
N-(4-{[3-(dimethylamino)pyrrolidin-1-yl]carbonyl}phenyl)biphenyl-4-carboxamide; 5-bromo-N-(4-{[3-(dimethylamino)pyrrolidin-1-yl]carbonyl}phenyl)thiophene-2-carboxamide;
4-cyclohexyl-N-(4-{[3-(dimethylamino)pyrrolidin-1-yl]carbonyl}phenyl)benzamide;
6-chloro-N-(4-{[3-(dimethylamino)pyrrolidin-1-yl]carbonyl}phenyl)-2H-chromene-3-carboxamide;
3-chloro-N-(4-{[3-(dimethylamino)pyrrolidin-1-yl]carbonyl}phenyl)-1-benzothiophene-2-carboxamide;
N-(4-{[3-(dimethylamino)pyrrolidin-1-yl]carbonyl}phenyl)-4-phenoxybenzamide;
N-(4-{[3-(dimethylamino)pyrrolidin-1-yl]carbonyl}phenyl)quinolin-5-amine;
1-[4-(2,3-dihydro-1,4-benzodioxin-6-ylamino)benzoyl]-N,N-dimethylpyrrolidin-3-amine;
1-[4-(1,3-benzodioxol-5-ylamino)benzoyl]-N,N-dimethylpyrrolidin-3-amine;
(3'S)-1'-(4-phenoxybenzoyl)-1,3'-bipyrrolidine;
(3'S)-1'-[4-(4-fluorophenoxy)benzoyl]-1,3'-bipyrrolidine;
(3'S)-1'-[4-(4-fluoro-2-methylphenoxy)benzoyl]-1,3'-bipyrrolidine;
(3'S)-1'-[4-(3-chloro-4-fluorophenoxy)benzoyl]-1,3'-bipyrrolidine;
(3'S)-1'-[4-(3-fluorophenoxy)benzoyl]-1,3'-bipyrrolidine;
(3'S)-1'-[4-(2-chloro-4-fluorophenoxy)benzoyl]-1,3'-bipyrrolidine;
4-{4-[(3'S)-1,3'-bipyrrolidin-1'-ylcarbonyl]phenoxy}quinoline;
(3'S)-1'-{4-[4-(1H-imidazol-1-yl)phenoxy]benzoyl}-1,3'-bipyrrolidine;
4-{4-[(3'S)-1,3'-bipyrrolidin-1'-ylcarbonyl]phenoxy}benzonitrile;
(3'S)-1'-[4-(3-methylphenoxy)benzoyl]-1,3'-bipyrrolidine;
(3'S)-1'-[4-(4-methylphenoxy)benzoyl]-1,3'-bipyrrolidine;
(3'S)-1'-[4-(3-methoxyphenoxy)benzoyl]-1,3'-bipyrrolidine;
(3'S)-1'-[4-(4-chlorophenoxy)benzoyl]-1,3'-bipyrrolidine;
(3'S)-1'-[4-(4-methoxyphenoxy)benzoyl]-1,3'-bipyrrolidine;
(3'S)-1'-[4-(4-chloro-2-methylphenoxy)benzoyl]-1,3'-bipyrrolidine;
(3'S)-1'-[4-(2-chloro-4-methylphenoxy)benzoyl]-1,3'-bipyrrolidine;
(3'S)-1'-[4-(2-methylphenoxy)benzoyl]-1,3'-bipyrrolidine;
(3'S)-1'-{4-[4-(4-fluorophenoxy)phenoxy]benzoyl}-1,3'-bipyrrolidine;
(3'S)-1'-{4-[3-(3-fluorophenoxy)phenoxy]benzoyl}-1,3'-bipyrrolidine;
(3'S)-1'-{4-[(4-chloro-1-napthyl)oxy]benzoyl}-1,3'-bipyrrolidine; or a stereoisomer thereof; or a pharmaceutically acceptable salt thereof.

Advantageously, the present invention provides a process to prepare compounds of formula I wherein X is CO (Ia) which comprises reacting a benzoic acid or benzoyl chloride compound of formula II with a pyrrolidine of formula III in the presence of a base optionally in the presence of a solvent. The reaction is shown in scheme I wherein Z is OH or Cl.

SCHEME I

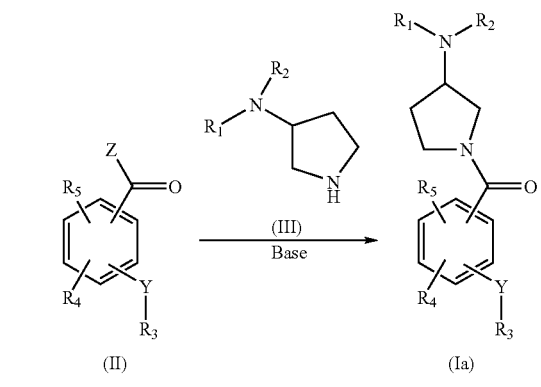

Bases suitable for use in the method of invention are organic amines such as triethylamine, methyldiethylamine, diisopropylethylamine or any suitable organic base useful as an acid scavenger in organic synthetic procedures. Solvents suitable for use in the method of the invention include methylene chloride, chloroform, tetrahydrofuran or the like.

Compounds of formula I wherein X is $CH_2$ (Ib) may be readily prepared by reacting the formula Ia compound with a suitable reducing agent such as $LiAlH_4$ or Borane to give the desired compound of formula Ib. The reaction is shown in scheme II.

SCHEME II

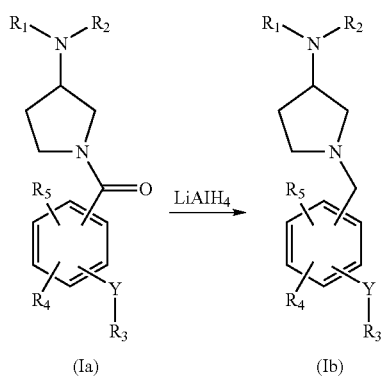

Compounds of formula I wherein X is $SO_2$ (Ic) may be prepared a manner similar to that described in reaction scheme I by replacing the benzoic acid or benzoyl chloride of formula II with the corresponding phenyl sulfonyl chloride of formula IV. For example the phenylsulfonyl chloride of formula IV may be reacted with a 3-aminopyrrolidine of formula III to give the desired compound of formula Ic. The reaction is shown in scheme III.

SCHEME III

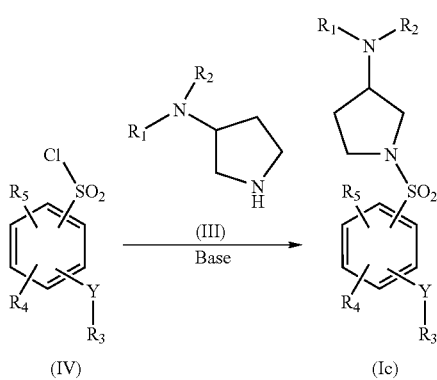

Similarly, compounds of formula I wherein X is S or SO may be prepared by reducing the compound of formula Ic with a suitable reducing agent to give the corresponding sulfinyl or thio compounds of formula I.

Alternatively, compounds of formula I wherein X is CO and Y is $NR_6$ (Id) may be prepared by reacting a bromobenzoyl chloride of formula Va with a pyrrolidin-3-ylamine of formula II in the presence of base such as diisopropylethylamine (DIEA) to give the compound of formula VII and reacting said formula VI compound with an amine of formula VII in the presence of a palladium coupling agent to give the desired formula Id compound. The reaction is shown in scheme IV.

SCHEME IV

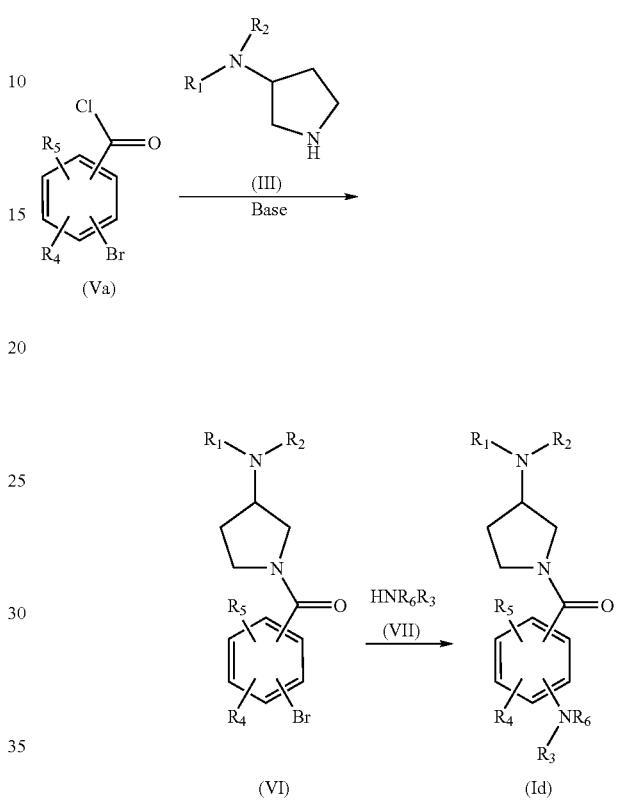

Compounds of formula Id wherein $R_6$ is H (Ie) may also be prepared by reacting a nitrobenzoyl compound of formula VIII with a pyrrolidin-3-ylamine of formula III in the presence of a DIEA and a solvent such as tetrahydrofuran to give the compound of formula IX; reducing the formula IX compound via catalytic hydrogenation to give the compound of formula X: and reacting the formula X compound with an aryl halide of formula XI in the presence of a catalyst such as pyridine HCl or a palladium catalyst. The reaction is shown in scheme V wherein Z is Cl or OH and Hal represents Cl, Br or I.

SCHEME V

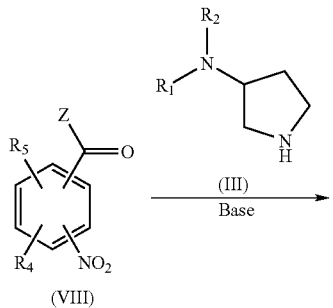

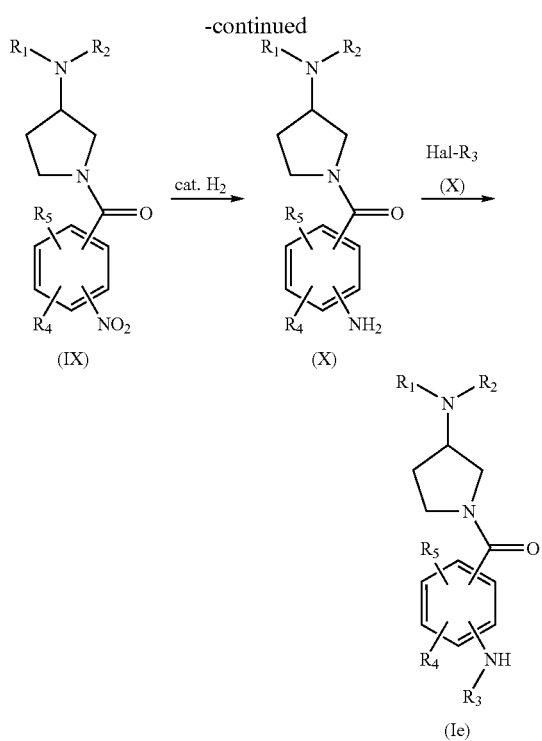

Compounds of formula I wherein X is CO and Y is NHCO (If) may be prepared in a manner similar to that described hereinabove. For example, a compound of formula X may be reacted with an aryl acid or an aryl acid chloride of formula XII in the presence of a base to give the desired compound of formula If. In addition to the aryl acid and aryl acid chloride, a mixed anydride may also be used. The reaction is shown in scheme VI wherein Z is OH or Cl.

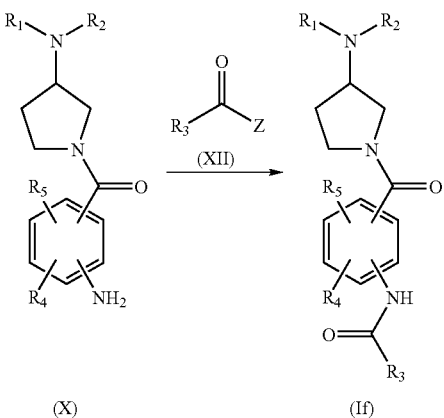

SCHEME VI

Advantageously, the formula I compounds of the invention are useful for the treatment of CNS disorders related to or affected by the Histamine-3 receptor including cognitive disorders, for example Alzheimer's disease, mild cognitive impairment, attention deficit hyperactivity disorder, schizophrenia, memory loss, sleep disorders, obesity or the like. Accordingly, the present invention provides a method for the treatment of a disorder of the central nervous system related to or affected by the Histamine-3 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The term "providing" as used herein with respect to providing a compound or substance embraced by the invention, designates either directly administering such a compound or substance, or administering a prodrug, derivative or analog which forms an equivalent amount of the compound or substance within the body.

The inventive method includes: a method for the treatment of schizophrenia; a method for the treatment of a disease associated with a deficit in memory, cognition or learning or a cognitive disorder such as Alzheimer's disease or attention deficit hyperactivity disorder; a method for the treatment of a mild cognitive disorder, a method for the treatment of a developmental disorder such as schizophrenia; a method for the treatment of a sleep disorder or any other CNS disease or disorder associated with or related to the H3 receptor.

In one embodiment, the present invention provides a method for treating attention deficit hyperactivity disorders (ADHD, also known as Attention Deficit Disorder or ADD) in both children and adults. Accordingly, in this embodiment, the present invention provides a method for treating attention deficit disorders in a pediatric patient.

The present invention therefore provides a method for the treatment of each of the conditions listed above in a patient, preferably in a human, said method comprises providing said patient a therapeutically effective amount of a compound of formula I as described hereinabove. The compounds may be provided by oral or parenteral administration or in any common manner known to be an effective administration of a therapeutic agent to a patient in need thereof.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

In one embodiment, the invention relates to compositions comprising at least one compound of formula I, or a pharmaceutically acceptable salt thereof, and one or more pharmaceutically acceptable carriers, excipients, or diluents. Such compositions include pharmaceutical compositions for treating or controlling disease states or conditions of the central nervous system. In certain embodiments, the compositions comprise mixtures of one or more compounds of formula I.

In certain embodiments, the invention relates to compositions comprising at least one compound of formula I, or a pharmaceutically acceptable salt thereof, and one or more pharmaceutically acceptable carriers, excipients, or diluents. Such compositions are prepared in accordance with acceptable pharmaceutical procedures. Pharmaceutically acceptable carriers are those carriers that are compatible with the other ingredients in the formulation and are biologically acceptable.

The compounds of formula I may be administered orally or parenterally, neat, or in combination with conventional pharmaceutical carriers. Applicable solid carriers can include one or more substances that can also act as flavoring agents, lubricants, solubilizers, suspending agents, fillers, glidants, compression aids, binders, tablet-disintegrating agents, or encapsulating materials. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

In certain embodiments, a compound of formula I is provided in a disintegrating tablet formulation suitable for pediatric administration.

Liquid carriers can be used in preparing solutions, suspensions, emulsions, syrups and elixirs. The active ingredient can be dissolved or suspended in a pharmaceutically acceptable liquid carrier such as water, an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

In certain embodiments, a liquid pharmaceutical composition is provided wherein said composition is suitable for pediatric administration. In other embodiments, the liquid composition is a syrup or suspension.

Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form.

The compounds of formula I may be administered rectally or vaginally in the form of a conventional suppository. For administration by intranasal or intrabronchial inhalation or insufflation, the compounds of formula I can be formulated into an aqueous or partially aqueous solution, which can then be utilized in the form of an aerosol. The compounds of formula I can also be administered transdermally through the use of a transdermal patch containing the active compound and a carrier that is inert to the active compound, is non-toxic to the skin, and allows delivery of the agent for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable. A variety of occlusive devices can be used to release the active ingredient into the blood stream such as a semipermeable membrane covering a reservoir containing the active ingredient with or without a carrier, or a matrix containing the active ingredient. Other occlusive devices are known in the literature.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The therapeutically effective amount of a compound of formula I provided to a patient will vary depending upon what is being administered, the purpose of the administration, such as prophylaxis or therapy, the state of the patient, the manner of administration, or the like. In therapeutic applications, compounds of formula I are provided to a patient suffering from a condition in an amount sufficient to treat or at least partially treat the symptoms of the condition and its complications. An amount adequate to accomplish this is a "therapeutically effective amount" as described previously herein. The dosage to be used in the treatment of a specific case must be subjectively determined by the attending physician. The variables involved include the specific condition and the size, age, and response pattern of the patient. Generally, a starting dose is about 5 mg per day with gradual increase in the daily dose to about 150 mg per day, to provide the desired dosage level in the patient.

In certain embodiments, the present invention is directed to prodrugs of compounds of formula I. The term "prodrug," as used herein, means a compound that is convertible in vivo by metabolic means (e.g. by hydrolysis) to a compound of formula I. Various forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991), Bundgaard, et al., Journal of Drug Delivery Reviews, 8:1-38 (1992), Bundgaard, J. of Pharmaceutical Sciences, 77:285 et seq. (1988); and Higuchi and Stella (eds.) Prodrugs as Novel Drug Delivery Systems, American Chemical Society (1975).

For a more clear understanding, and in order to illustrate the invention more clearly, specific examples thereof are set forth hereinbelow. The following examples are merely illustrative and are not to be understood as limiting the scope and underlying principles of the invention in any way. The terms HPLC and NMR designate high performance liquid chromatography and proton nuclear magnetic resonance, respectively. The term MS designates mass spectroscopy with (+) referring to the positive mode which generally gives a M+1 (or M+H) absorption where M=the molecular mass. All compounds are analyzed at least by MS and NMR. The term Boc designates t-butoxycarbonyl. The terms EtOAc, DMSO and THF designate ethyl acetate, dimethylsulfoxide and tetrahydrofuran, respectively. Unless otherwise noted, all parts are parts by weight.

EXAMPLE 1

Preparation of 1'-(4-phenoxybenzoyl)-1,3'-bipyrrolidine Hydrochloride

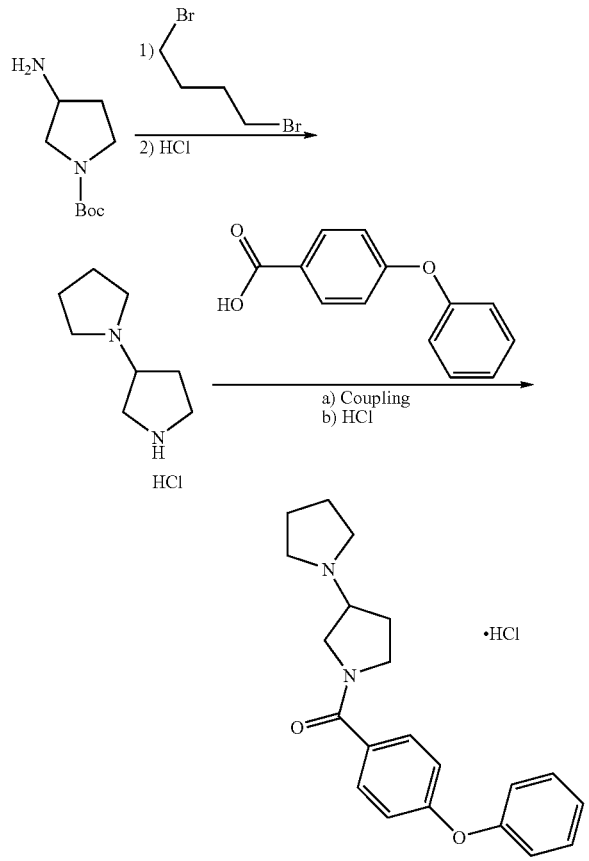

Step 1. Boc-protected 3-aminopyrrolidine (1 mL, 11.6 mmol) is mixed with 1,4-dibromobutane (1.2 eq. 1.7 mL) and K$_2$CO$_3$ (2 eq) in toluene and heated to reflux temperature for 16 h. The reaction mixture is cooled to room temperature, diluted with EtOAc, washed with water, dried over MgSO$_4$ and evaporated in vacuo to give a residue.

Step 2. The residue (1 g, crude, about 4.2 mmol, theory) is stirred with 2 N HCl in dioxane for 3 h, until the deprotection is complete. The reaction mixture is filtered to give the 3-(pyrrolidino)pyrrolidine HCl salt product in its crystalline form.

Step 3. A stirred mixture of the HCl salt of 3-(pyrrolidino) pyrrolidine (0.44 g, 2.1 mmol) and 4-phenoxy benzoic acid (0.34 g, 1.6 mmol) in CH$_2$Cl$_2$ is treated with 0.85 mL of triethylamine at room temperature. The reaction mixture is treated with solid benzotriazol-1-yl-oxytripyrrolidinophosphonium hexafluorophosphate (1.2 g, 2.4 mmol), stirred overnight under nitrogen, diluted with CH$_2$Cl$_2$, washed sequentially with water and brine, dried over MgSO$_4$ and concentrated in vacuo. The resultant residue is chromatographed and treated with HCl in ether to afford the title compound as a white solid, identified by NMR and MS analyses.

EXAMPLE 2

Preparation of 1-(4-Aminobenzoyl)-3-dimethylamino-pyrrolidine

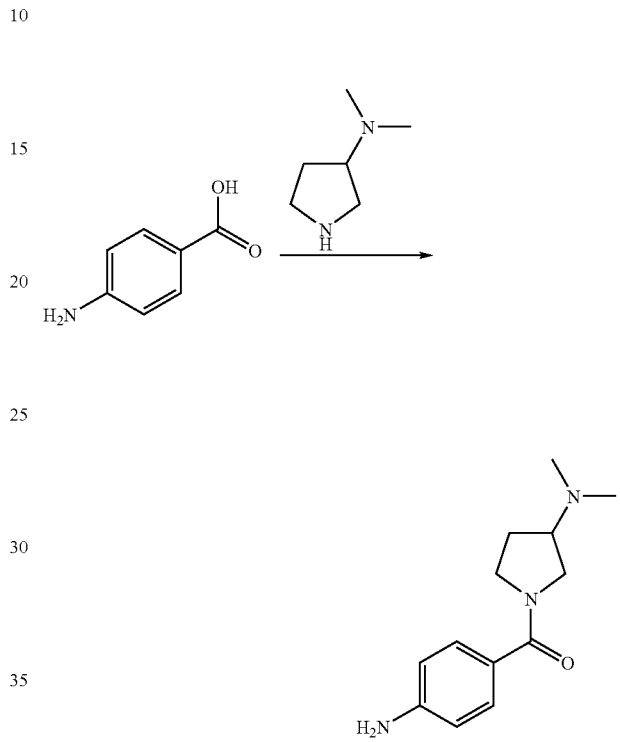

A mixture of 4-aminobenzoic acid (1.4 g, 10 mmol), 3-(dimethylamino)-pyrrolidine (1.5 g, 13 mmol) and 1-(3-dimethylaminopropyl)-3-ethylcarbodiimide (2.5 g, 13 mmol) in CH$_2$Cl$_2$ is stirred at room temperature for 16 h, diluted with CH$_2$Cl$_2$, washed with water, dried over MgSO$_4$ and concentrated in vacuo to give the title compound (1.1 g), identified by NMR analysis.

EXAMPLE 3

Preparation of N-(4-{[3-(Dimethylamino)pyrrolidin-1-yl]carbonyl}phenyl)-2-phenylquinazolin-4-amine

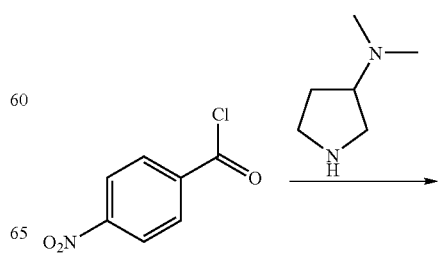

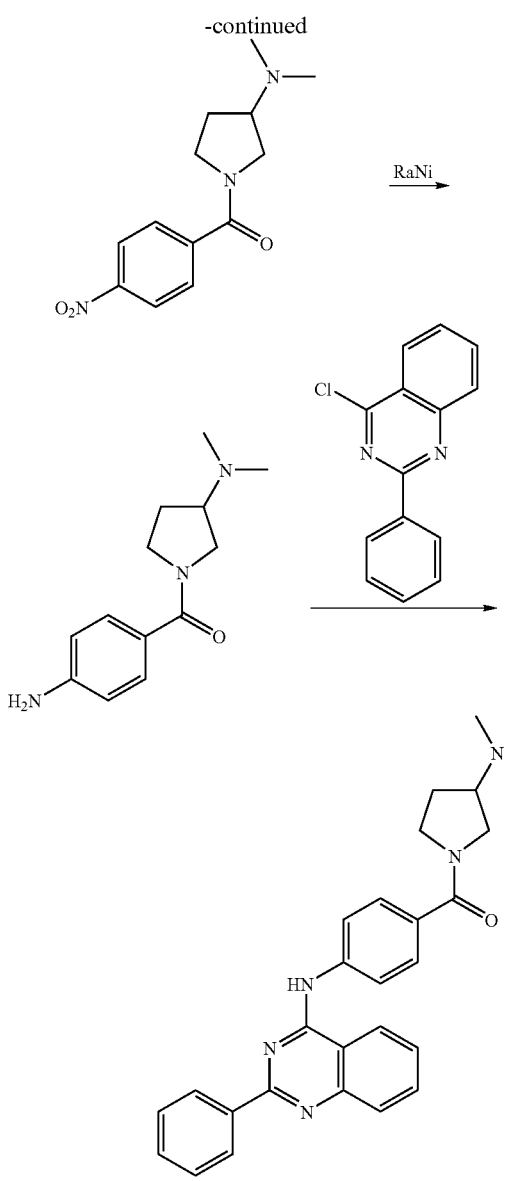

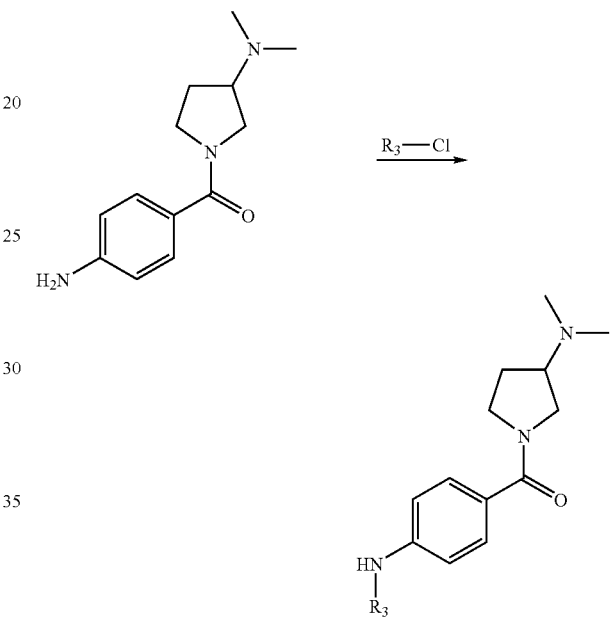

vacuo. The resultant residue is dissolved in a mixture of DMSO, methanol and water and purified by reverse-phase semi-preparative HPLC[1] to give the title product as a white powder (15 mg), identified by HPLC and mass spectral analyses. Retention Time, 2.69 min.; MS [438.2 m/e (M+H)].

[1] Semi-preparative HPLC Conditions: A=0.02% TFA in water, B=0.02% TFA in acetonitrile, 10-95% B in 8 min., 34 mL/min, 50° C., 215 nm detection, Waters Xterra™ 20×50 mm column.

EXAMPLES 4-10

Preparation of N-(4-{[3-(Dimethylamino)pyrrolidin-1-yl]carbonyl}phenyl)-heteroaryl-4-amine Compounds Using essentially the same procedure described in Example 2, Step 3, and employing the appropriate heteroaryl chloride, $R_3$—Cl, the compounds shown in Table I are obtained and identified by HPLC and mass spectral analyses. HPLC Conditions are the same as those used in Example 3.

Step 1. To a solution of 4-nitrobenzoyl chloride (1.8 g, 10 mmol) and diisopropylethylamine (2.8 mL, 20 mmol) in THF at room temperature is added 3-(dimethylamino)pyrrolidine (1.4 mL, 11 mmol). The reaction is stirred for 2 hours at room temperature and concentrated in vacuo to give 3-dimethylamino-1-(4-nitrobenzoyl)pyrrolidine, identified by HPLC and MS [264.3 m/e (M+H)] analyses.

Step 2. The 3-dimethylamino-1-(4-nitrobenzoyl)pyrrolidine (2.4 g, crude), obtained in Step 1, is dissolved in methanol, treated sequentially with hydrazine (5 mL) and Raney-Nickel (suspension in water, approximately 1 g), stirred at room temperature for 4 h and filtered through celite. The filtercake is washed with methanol. The filtrates are combined and concentrated to give 1-(4-aminobenzoyl)-3-dimethylamino-pyrrolidine as a pale brown oil, identified by HPLC and MS [234.5 m/e (M+H)].

Step 3. A mixture of 1-(4-aminobenzoyl)-3-dimethylamino-pyrrolidine (46 mg, 0.2 mmol), 4-chloro-2-phenylquinazoline (48 mg, 0.2 mmol) and pyridine hydrochloride (23 mg, 0.2 mmol) in ethoxyethanol is heated to 135° C. overnight, cooled to room temperature and concentrated in

TABLE I

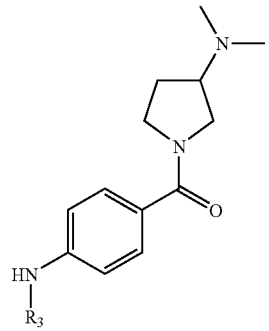

| Ex. No. | R3 | [M + H] | Time (Min.) |
|---|---|---|---|
| 4 | 9-H-purin-6-yl | 350.2 | 1.70 |
| 5 | pyridin-2-yl | 311.5 | 1.36 |
| 6 | thieno[2,3-d]pyrimidin-4-yl | 368.1 | 1.99 |

TABLE I-continued

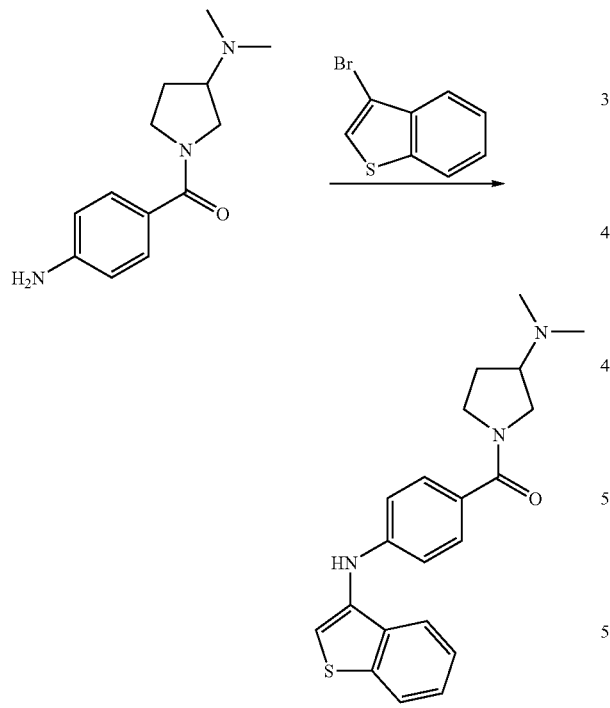

| Ex. No. | R3 | [M + H] | Time (Min.) |
|---|---|---|---|
| 7 | 7-methyl-thieno[2,3-d]pyrimidin-4-yl | 382.2 | 2.13 |
| 8 | isoquinolin-1-yl | 361.2 | 2.49 |
| 9 | 5-(trifluoromethyl)pyridin-2-yl | 377.2 | 2.62 |
| 10 | pyrimidin-2-yl | 312.2 | 1.91 |

EXAMPLE 11

Preparation of 1-[4-(1-Benzothien-3-ylamino)benzoyl]-N,N-dimethylpyrrolidin-3-amine A mixture of 1-(4-aminobenzoyl)-3-dimethylamino-pyrrolidine (50 mg, 0.21 mmol), 3-bromobenzothiophene (50 mg, 0.23 mmol), sodium tert-butoxide (44 mg, 34 mmol), tris(dibenzylideneacetone)dipalladium(0) (3 mg, 0.002 mmol), CTC-Q-Phos (6 mg, 0.004 mmol) is heated to 80° C. for 16 h and concentrated in vacuo. The resultant residue is dissolved in a mixture of DMSO, methanol and water and purified by reverse-phase semi-preparative HPLC[1] to give the title compound as a white powder (11 mg), identified by HPLC and mass spectral analyses. Retention Time, 2.62 min.; MS [366.2 m/e (M+H)].

[1] Semi-preparative HPLC Conditions: A=0.02% TFA in water, B=0.02% TFA in acetonitrile, 10-95% B in 8 min., 34 mL/min, 50° C., 215 nm detection, Waters Xterra™ 20×50 mm column.

EXAMPLE 12

Preparation of N-(4-[{3-(Dimethylamino)pyrrolidin-1-yl]carbonyl}phenyl)-2,1,3-benzothiadiazol-4-amine

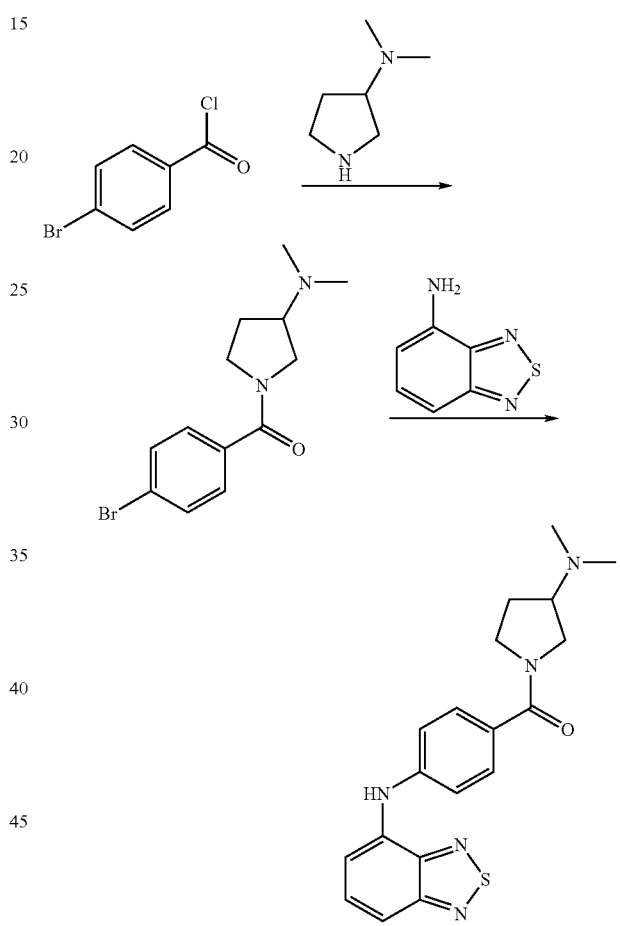

Step 1. To a solution of 4-bromobenzoyl chloride (2.2 g, 10 mmol) and pyridine (1 mL) in $CH_2Cl_2$ at 0° C. is added 3-(dimethylamino)pyrrolidine (1.14 mL, 10 mmol). The reaction is stirred at room temperature for 2 h, diluted with ether and filtered. The filtercake is washed with ether, treated with 0.1 N sodium hydroxide, stirred and filtered. This filtercake is washed with ether and recrystallized from petroleum ether to give 1-(4-bromobenzoyl)-3-dimethylaminopyrrolidine as a white powder (1.5 g), identified by NMR analysis.

Step 2. A mixture of 1-(4-bromobenzoyl)-3-dimethylaminopyrrolidine (40 mg, 0.13 mmol), 4-amino-2,1,3-benzothiadiazole (23 mg, 0.13 mmol), potassium phosphate (27 mg, 0.13 mmol), tris(dibenzylideneacetone)dipalladium(0) (3 mg, 0.002 mmol), and CTC-Q-Phos (6 mg, 0.004 mmol) are heated to 80° C. for 16 h and concentrated in vacuo. The resultant residue is dissolved in a mixture of DMSO, methanol and water and purified by reverse-phase semi-preparative HPLC[1] to give the title compound as a white powder (11 mg), identified by HPLC and mass spectral analyses. Retention Time, 1.74 min.; MS [368.6 m/e (M+H)].

[1]Semi-preparative HPLC Conditions: A=0.02% TFA in water, B=0.02% TFA in acetonitrile, 10-95% B in 8 min., 34 mL/min, 50° C., 215 nm detection, Waters Xterra™ 20×50 mm column.

EXAMPLES 13-16

Preparation of N-(4-{[3-(Dimethylamino)pyrrolidin-1-yl]carbonyl}phenyl)-heteroaryl-4-amine Compounds

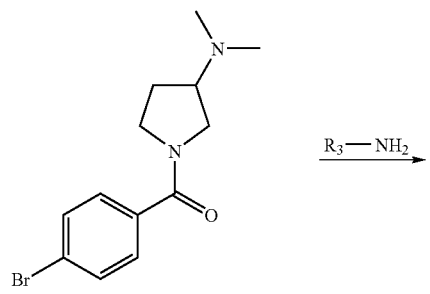

Using essentially the same procedure described in Example 12, Step 2, and employing the appropriate heteroarylamine, $R_3$—$NH_2$, the compounds shown in Table II are obtained and identified by HPLC and mass spectral analyses. HPLC Conditions are the same as those used in Example 12.

TABLE II

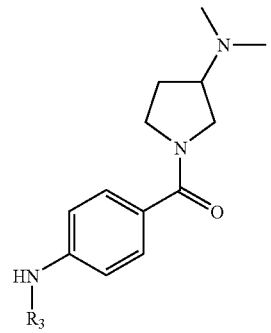

| Ex. No. | R3 | [M + H] | Time (Min.) |
|---|---|---|---|
| 13 | 1-H-indol-5-yl | 349.2 | 2.51 |
| 14 | quinolin-5-yl | 361.2 | 2.18 |

TABLE II-continued

| Ex. No. | R3 | [M + H] | Time (Min.) |
|---|---|---|---|
| 15 | 2,3-dihydrobenzodioxin-6-yl | 368.2 | 1.68 |
| 16 | 1,3-benzodioxol-5-yl | 354.2 | 2.48 |

EXAMPLE 17

Preparation of N-(4-{[3-(dimethylamino)pyrrolidin-1-yl]carbonyl}phenyl)quino-line-2-carboxamide

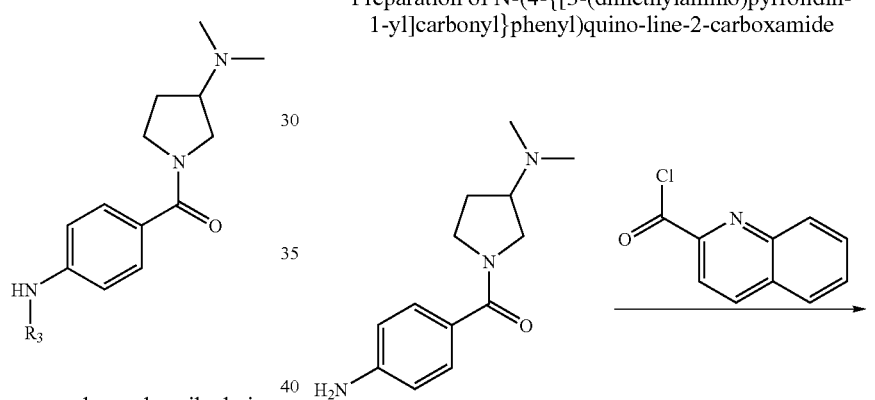

A mixture of 1-(4-aminobenzoyl)-3-dimethylamino-pyrrolidine (46 mg, 0.2 mmol), quinoline-2-carbonyl chloride (38 mg, 0.2 mg) and diisopropyl ethyl amine (0.1 mL, 0.6 mmol) in $CH_2Cl_2$ is stirred at room temperature for 5 h and concentrated in vacuo. The resultant residue is dissolved in a mixture of DMSO, methanol and water and purified by reverse-phase semi-preparative HPLC, using the same HPLC conditions described in Example 1, to give the title compound as a white powder (10mg), identified by HPLC and mass spectral analyses. Retention Time, MS [366.2 m/e (M+H)].

EXAMPLES 18-33

Preparation of N-(4-{[3-(dimethylamino)pyrrolidin-1-yl]carbonyl}phenyl)aryl- and -heteroaryl-carboxamide Compounds

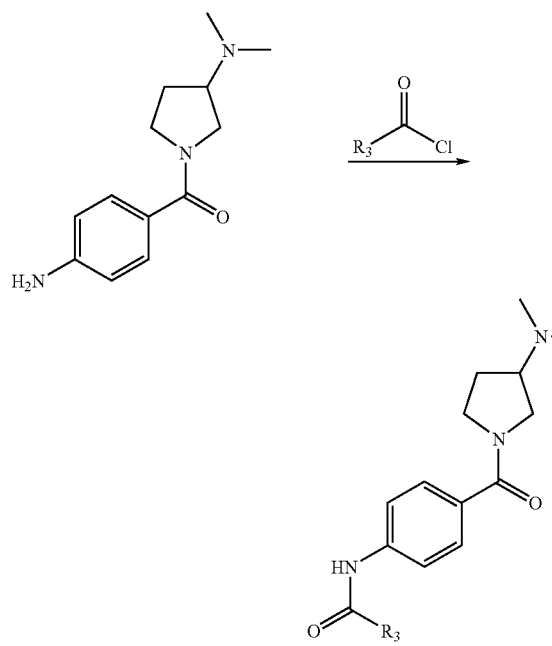

Using essentially the same procedure described in Example 17 and employing the desired aryl or heteroaryl acid chloride, the compounds shown in Table III are obtained and identified by NMR and mass spectral analyses. The HPLC conditions are the same as those described in Example 1.

TABLE III

| Ex. No. | R3 | [M + H] | Time (Min.) |
|---|---|---|---|
| 18 | naphth-1-yl | 388.6 | 2.44 |
| 19 | benzothiophene-2-yl | 394.6 | 2.25 |
| 20 | thiophene-2-yl | 378.1 | 1.64 |
| 21 | naphth-2-yl | 388.2 | 1.82 |
| 22 | isoquin-1-yl | 389.2 | 1.75 |
| 23 | 1-H-indol-2-yl | 391.2 | 1.82 |
| 24 | 1,2,3,4-tetrahydronaphth-2-yl | 392.2 | 1.86 |
| 25 | 5-methyl-3-phenyl-isoxazol-4-yl | 419.2 | 1.66 |
| 26 | 4-methoxyquinolin-2-yl | 419.2 | 1.92 |
| 27 | 7-methoxy-benzofuran-2-yl | 408.2 | 1.79 |

TABLE III-continued

| Ex. No. | R3 | [M + H] | Time (Min.) |
|---|---|---|---|
| 28 | 4-biphenyl | 414.2 | 1.92 |
| 29 | 5-bromothiophene-2-yl | 422 | 1.77 |
| 30 | 4-cyclohexylphenyl | 420.3 | 2.16 |
| 31 | 6-chloro-2H-chromene-3-yl | 426.2 | 1.92 |
| 32 | 3-chlorobenzothiophene-2-yl | 428.1 | 1.92 |
| 33 | 4-phenoxyphenyl | 430.2 | 1.92 |

EXAMPLE 34

Preparation of (3'S)-1'-[4-(3-Methylhenoxy)benzoyl]-1,3'-bipyrrolidine Hydrochloride

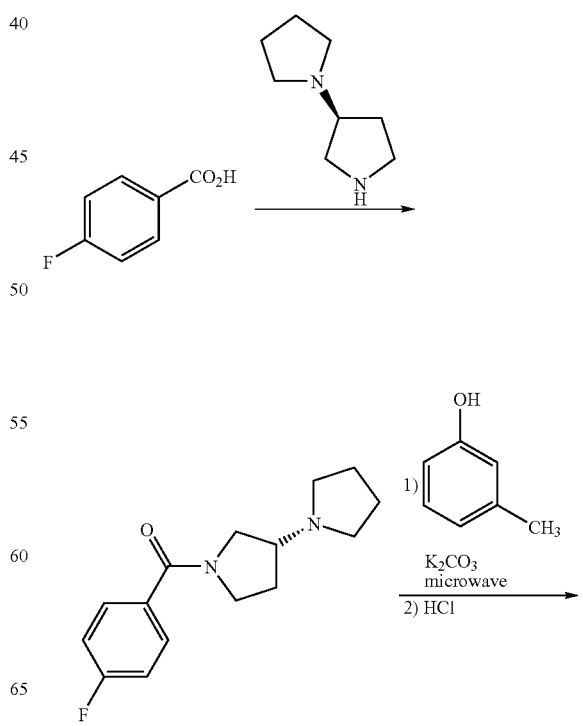

-continued

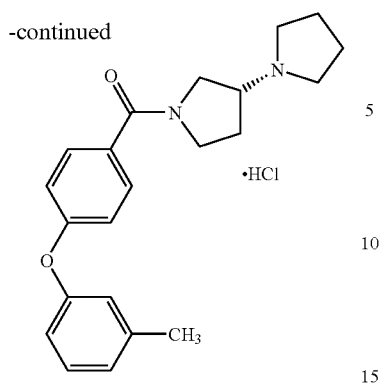

Step 1) (3'S)-1'-(4-fluorobenzoyl)-1,3'-bipyrrolidine

A solution of 4-fluorobenzoic acid (1.5 g, 10.71 mmol) in dichloroethane:DMF (4:1) was treated with O-benzotriazol-1-yl-N,N,N'N'-tetramethlyuronium tetrafluoroborate (4.13 gm 12.85 mmol) and N-methylmorpholine (5.41 g, 53.55 mmol) followed by a solution of (3'S)-1,3'-bipyrrolidine (2.52 g, 11.77 mmol) in dichloroethane:DMF (4:1). The reaction mixture was stirred at room temperature for 3 h and quenched with saturated sodium hydrogen carbonate. The phases were separated. The aqueous phase was extracted with ethyl acetate. The organic phase and the extracts were combined, washed sequentially with water and saturated aqueous sodium chloride, dried over magnesium sulfate and concentrated in vacuo. The resultant residue was purified by flash column chromatography to provide (3'S)-1'-(4-fluorobenzoyl)-1,3'-bipyrrolidine (57%) as a white solid.

Step 2) (3'S)-1'-[4-(3-methylphenoxy)benzoyl]-1,3'-bipyrrolidine hydrochloride

A solution of (3'S)-1'-(4-fluorobenzoyl)-1,3'-bipyrrolidine (0.011 g, 0.381 mmol in dimethylformamide was treated with m-cresol (0.127 g, 1.14 mmol) and potassium carbonate (0.105 g, 0.762 mmol), heated to 150° C. via microwave radiation for 20 minutes and cooled to room temperature. The reaction mixture was diluted with dichloromethane, washed sequentially with water and saturated aqueous sodium chloride, dried over magnesium sulfate and concentrated in vacuo. The resultant residue was purified by flash column chromatography (silica, methanol:dichloromethane 5:95) to give the free amine of the title product as a yellow oil. This oil was dissolved in isopropanol and diethyl ether (1:10), treated with 1.0N HCl in diethyl ether and filtered. The filter cake was dried to afford the title product as a yellow solid, 0.021 g (16%), identified by NMR and mass spectral analyses. MS [351.3 m/e (M+H)].

EXAMPLES 35-43

Preparation of (3'S)-1'-[4-(Substituted-phenoxy)benzoyl]-1,3'-bipyrrolidine Hydrochloride Compounds

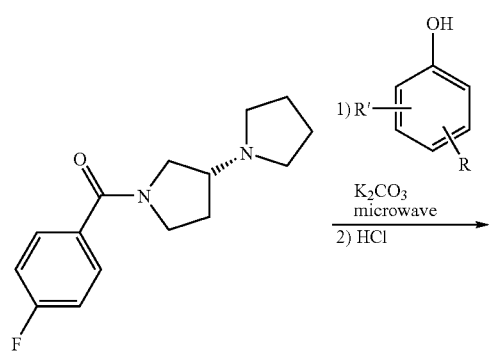

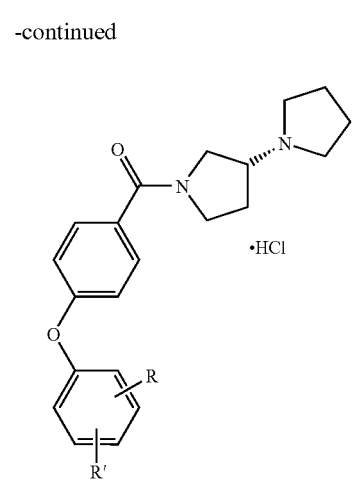

Using essentially the same procedure described in Example 34, Step 2, and employing the desired phenol, the compounds shown on Table IV were obtained and identified by NMR and mass spectral analyses.

TABLE IV

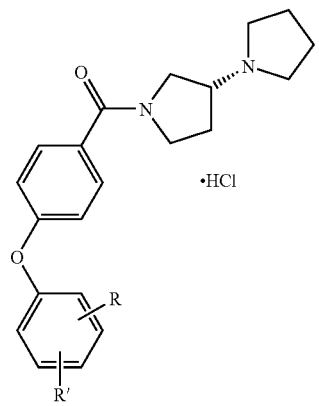

| Ex. No. | R | R' | % Yield | mp ° C. | [M + H] |
|---|---|---|---|---|---|
| 35 | H | 4-CH$_3$ | 34 | 98-100 | 351.3 |
| 36 | H | 3-OCH$_3$ | 34 | 82-84 | 367.2 |
| 37 | H | 4-Cl | 21 | — | 371.2 |
| 38 | H | 4-OCH$_3$ | 16 | — | 367.2 |
| 39 | 2-CH$_3$ | 4-Cl | 35 | 123-125 | 385.2 |
| 40 | 2-Cl | 4-CH$_3$ | 33 | 124-126 | 385.2 |
| 41 | 2-CH$_3$ | H | 9 | — | 351.3 |
| 42 | H | 4-imidazol-1-yl | 28 | — | 403.2 |
| 43 | H | 4-CN | 12 | — | 362.3 |

EXAMPLE 44

Preparation of (3'S)-1'-(4-phenoxybenzoyl)-1,3'-bipyrrolidine Hydrochloride

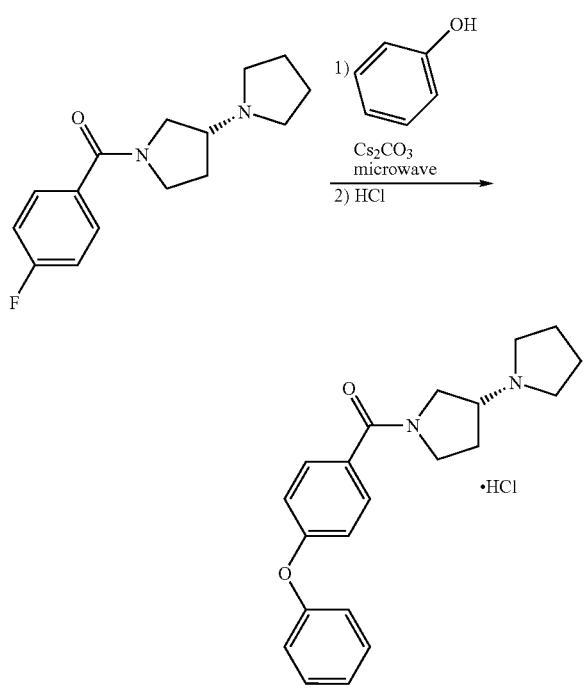

A mixture of 100 mg of (3'S)-1'-(4-fluorobenzoyl)-1,3'-bipyrrolidine (0.4 mmol), 1.5 equivalents of phenol and 2.0 equivalents of cesium carbonate in 1 mL of DMF is irradiated in a CEM Microwave vessel for 10 minutes. The reaction mixture is cooled to room temperature and purified by Gilson reverse phase chromatography to afford the free amine of the title product. The free amine is treated with ethereal HCl and evaporated to dryness in vacuo to give the title product, identified by NMR and mass spectral analyses. [M+H] 337.4

EXAMPLES 45-53

Preparation of (3'S)-1'-(4-phenoxybenzoyl)-1,3'-bipyrrolidine

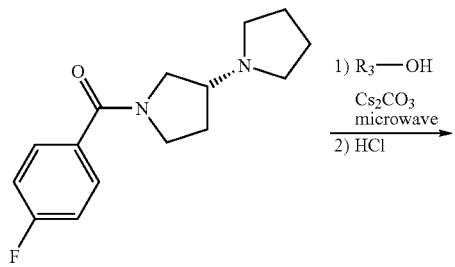

-continued

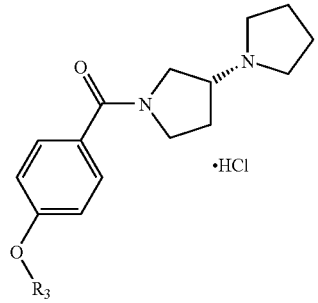

Using essentially the same procedure described in Example 44 and employing the desired substituted phenol reagent, the compounds shown on Table V were obtained and identified by NMR and mass spectral analyses.

TABLE V

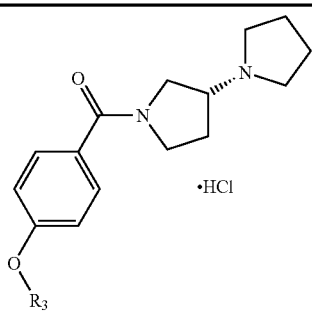

| Ex. No. | R3 | [M + H] |
|---|---|---|
| 45 | 4-fluorophenyl | 355.2 |
| 46 | 4-fluoro-2-methylphenyl | 369.4 |
| 47 | 3-chloro-4-fluorophenyl | 389.9 |
| 48 | 3-fluorophenyl | 355.4 |
| 49 | 2-chloro-4-fluorophenyl | 389.9 |
| 50 | quinolin-4-yl | 388.5 |
| 51 | 4-chloronaphth-1-yl | 421.9 |
| 52 | 4-(4-fluorophenoxy)phenyl* | 447.5 |
| 53 | 3-(3-fluorophenoxy)phenyl* | 447.5 |

*Isolated as a byproduct when displacement of fluoride occurred more than once.

EXAMPLE 54

Evaluation of Methyl Histamine Binding in Human Histamine H3 Receptor Cell Line

The affinity of test compounds for the histamine 3 (H3) receptor is evaluated in the following manner. Stably transfected HEK293T cells are grown in DMEM containing 10% heat inactivated FBS and G-418 (500 ug/ml). Cells are scraped from the plate, transferred to centrifuge tubes, washed one time in PBS by centrifugation in a Sorvall RT7 Plus centrifuge (2000 rpm 10 minutes, 4° C.). The resulting pellets are stored at −80° C. until ready for use. Cells are re-suspended in buffer (50 mM Tris pH=7.5) and placed in a Dounce homogenizer, douncing ten times to homogenize cells. The homogenate is spun down by centrifugation (Sorvall RT7 Plus, 1800 rpm 10 minutes, 4° C.). The supernatant is placed in a Corex tube and spun down by centrifugation (Sorvall RC 5c Plus, 17,000 rpm 20 minutes, 4° C.). The pellet is resuspended in buffer (50 mM Tris, pH 7.5). Protein concentration (ug/ul) is determined using the Micro-BCA Protein Determination. The binding assay is set up in a 96 well microtiter plate in a total volume of 250 uL. Non-specific binding is determined in the presence of 10 uM clobenpropit. The final radioligand concentration is 1 nM. The test compound is serially diluted using the Beckman Biomek2000 to a final approximate range of 100 uM to 100 pM. Membranes are suspended in buffer, homogenized in 2 bursts of ten seconds using a Vitris mechanical homogenizer set at power setting 5. Ten pg of membranes are added to each well. Following a one hour incubation at 30° C., the reaction is terminated by the addition of ice cold buffer and rapid filtration with a Packard Filtermate Harvester through a GF/B filter pre-soaked with 1% PEI for one hour. The plate is dried for one hour at 37° C. and 60 µL Microscint Scintillant is added to each well. The CPM per well is measured on a Packard Top Count NXT. Ki values are determined in nM. The Ki is calculated from the $IC_{50}$ (i.e. the concentration of competing ligand which displaces 50% of the specific binding of the radioligand). CPM values are expressed as % specific binding and plotted vs compound concentration. A curve is fitted using a four-parameter logistic fit and the $IC_{50}$ value is determined. The Ki is calculated from this using the Cheng-Prusoff equation: $pKi=IC_{50}/1+(L/Kd)$ where L=concentration of free radioligand used in the assay, and Kd is the dissociation constant of the radioligand for the receptor. L is determined for each experiment by counting an aliquot of the diluted radioligand (corresponding to that added to each well) and the Kd has previously been determined under identical conditions for this cell line/radioligand.

Cyclic AMP Assay for Histamine Receptor H3 Antagonism Activity.

Stable H3 cells are maintained in tissue culture flask in DMEM with high glucose, 10% FBS, 1×pen/strep, 500 ug/ml GY18, until experiment. Culture media is removed and cells are washed twice with PBS w/ Ca++ and Mg++ plus 500 µM IBMX. Cells are then detached by tapping on the side of the flask and resuspend in the same buffer. Two thousand cells/well are incubated with 1 µM histamine plus 10 µM forskolin plus various concentrations of compounds in a total volume of 30 µL in 96 well plates for 30 min at 30° C. Final test compound concentrations range from 10-4M to 10-9.5M at full log dilutions. Cyclic AMP levels are measured using HitHunter cAMP kit from Discoverx, cat# 900041 according to manufacturer's instruction. Chemiluminescence signals are detected using Top Count (Packard). Cyclic AMP levels in control cells receiving 10 µM forskolin plus 100 nM histamine are considered 0%, and in cells receiving 10 uM forskolin plus 100 nM histamine plus 1 µM clobenpropit are considered 100%. Data are expressed as % control and analyzed using Prizm software. The Kb values are calculated using the following equation, $KB=EC_{50}$ or $IC_{50}/[1+(ligand/Kd)]$. The data are shown in Table VI, below.

TABLE VI

| Ex No | H3 Binding Ki (nM) | cAMP Kb (nM) |
| --- | --- | --- |
| 1 | A | — |
| 3 | — | — |
| 4 | D | — |
| 5 | — | — |
| 6 | D | 10.8 |
| 7 | D | 14 |
| 8 | — | — |
| 9 | — | — |
| 10 | — | — |

TABLE VI-continued

| Ex No | H3 Binding Ki (nM) | cAMP Kb (nM) |
| --- | --- | --- |
| 11 | D | — |
| 12 | — | — |
| 13 | D | — |
| 14 | — | — |
| 15 | D | — |
| 16 | D | — |
| 17 | D | 57 |
| 18 | — | — |
| 19 | D | — |
| 20 | — | — |
| 21 | D | — |
| 22 | D | — |
| 23 | D | — |
| 24 | D | — |
| 25 | D | — |
| 26 | D | — |
| 27 | D | — |
| 28 | D | — |
| 29 | D | — |
| 30 | D | — |
| 31 | D | — |
| 32 | D | — |
| 33 | D | — |
| 34 | B | — |
| 35 | B | — |
| 36 | B | — |
| 37 | B | — |
| 38 | B | — |
| 39 | A | — |
| 40 | A | — |
| 41 | A | — |
| 42 | A | — |
| 43 | A | — |
| 44 | A | — |
| 45 | A | — |
| 46 | A | — |
| 47 | A | — |
| 48 | A | — |
| 49 | A | — |
| 50 | A | — |
| 51 | D | — |
| 52 | B | — |
| 53 | B | — |

What is claimed is:
1. A compound of formula I

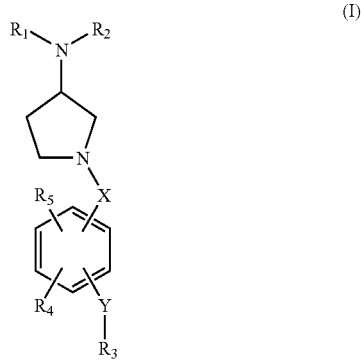

wherein
X is CO, $CH_2$ or $SO_m$;
Y is $NR_6$, $NR_6CO$, O or $SO_p$;
m and p are each individually 0 or an integer of 1 or 2;
$R_1$ and $R_2$ are taken together with the atom to which they are attached to form an optionally substituted 4- to 7-membered ring optionally containing one or two additional heteroatoms selected from N, O or S $R_3$ is an aryl group optionally substituted;

$R_4$ and $R_5$ are each independently H, halogen, $OR_9$ or an alkyl, alkenyl, alkynyl, cycloalkyl, cycloheteroalkyl, aryl or heteroaryl group each optionally substituted; and $R_6$ and $R_9$ are each independently H or an optionally substituted alkyl group; or a stereoisomer thereof or a pharmaceutically acceptable salt thereof.

2. The compound according to claim 1 wherein X is CO or $CH_2$.

3. The compound according to claim 1 wherein Y is $NR_6$, $NR_6CO$ or O.

4. The compound according to claim 1 wherein $R_1$ and $R_2$ are taken together with the atom to which they are attached to form an optionally substituted 5-membered ring.

5. The compound according to claim 2 wherein Y is O.

6. The compound according to claim 2 wherein $R_1$ and $R_2$ are taken together with the atom to which they are attached to form a 5-membered ring.

7. The compound according to claim 5 wherein $R_1$ and $R_2$ are taken together with the atom to which they are attached to form a 5-membered ring.

8. The compound according to claim 7 wherein X is CO.

9. The compound according to claim 1 selected from:
(3'S)-1'-(4-phenoxybenzoyl)-1,3'-bipyrrolidine;
(3'S)-1'-(4-phenobenzoyl)-1,3'-bipyrrolidine;
(3'S)-1'-[4-(4-fluorophenoxy)benzoyl]-1,3'-bipyrrolidine;
(3'S)-1'-[4-(4-fluoro-2-methylphenoxy)benzoyl]-1,3'-bipyrrolidine;
(3'S)-1'[4-(3-chloro-4-fluorophenoxy)benzoyl]-1,3'-bipyrrolidine;
(3'S)-1'[4-(3-fluorophenoxy)benzoyl]-1,3'-bipyrrolidine;
(3'S)-1'[4-(2-chloro-4-fluorophenoxy)benzoyl]-1,3'-bipyrrolidine;
4-{4-[(3'S)-1,3'-bipyrrolidin-1'-ylcarbonyl]phenoxy}benzonitrile;
(3'S)-1'[4-(3-methylphenoxy)benzoyl]-1,3'-bipyrrolidine;
(3'S)-1'[4-(4-methylphenoxy)benzoyl]-1,3'-bipyrrolidine;
(3'S)-1'[4-(3-methoxyphenoxy)benzoyl]-1,3'-bipyrrolidine;
(3'S)-1'[4-(4-chlorophenoxy)benzoyl]-1,3'-bipyrrolidine;
(3'S)-1'[4-(4-methoxyphenoxy)benzoyl]-1,3'-bipyrrolidine;
(3'S)-1'[4-(4-chloro-2-methylphenoxy)benzoyl]-1,3'-bipyrrolidine;
(3'S)-1'[4-(2-chloro-4-methylphenoxy)benzoyl]-1,3'-bipyrrolidine;
(3'S)-1'[4-(2-methylphenoxy)benzoyl]-1,3'-bipyrrolidine;
(3'S)-1'-{4-[4-(4-fluorophenoxy)phenoxy]benzoyl}-1,3'-bipyrrolidine;
(3'S)-1'-{4-[3-(3-fluorophenoxy)phenoxy]benzoyl}-1,3'-bipyrrolidine;
(3'S)-1'-{4-[(4-chloro-1-napthyl)oxy]benzoyl}-1,3'-bipyrrolidine;
a stereoisomer thereof; and
a pharmaceutically acceptable salt thereof.

10. A pharmaceutical composition comprising an effective amount of a compound of claim 1, a stereoisomer thereof or a pharmaceutically acceptable salt thereof, and a pharmaceutically acceptable carrier.

11. The composition according to claim 10 wherein X is CO or $CH_2$.

12. The composition according to claim 11 wherein $R_1$ and $R_2$ are taken together with the atom to which they are attached to form an optionally substituted 5-membered ring.

13. The composition according to claim 12 wherein Y is O.

14. The composition according to claim 10 selected from:
(3'S)-1'-(4-phenoxybenzoyl)-1,3'-bipyrrolidine;
(3'S)-1'-(4-phenoxybenzoyl)-1,3'-bipyrrolidine;
(3'S)-1'-[4-(4-fluorophenoxy)benzoyl]-1,3'-bipyrrolidine;
(3'S)-1'-[4-(4-fluoro-2-methylphenoxy)benzoyl]-1,3'-bipyrrolidine;
(3'S)-1'-[4-(3-chloro-4-fluorophenoxy)benzoyl]-1,3'-bipyrrolidine;
(3'S)-1'-[4-(3-fluorophenoxy)benzoyl]-1,3'-bipyrrolidine;
(3'S)-1'-[4-(2-chloro-4-fluorophenoxy)benzoyl]-1,3'-bipyrrolidine;
4-{4-[(3'S)-1,3'-bipyrrolidin-1'-ylcarbonyl]phenoxy}benzonitrile;
(3'S)-1'-[4-(3-methylphenoxy)benzoyl]-1,3'-bipyrrolidine;
(3'S)-1'-[4-(4-methylphenoxy)benzoyl]-1,3'-bipyrrolidine;
(3'S)-1'-[4-(3-methoxyphenoxy)benzoyl]-1,3'-bipyrrolidine;
(3'S)-1'-[4-(4-chlorophenoxy)benzoyl]-1,3'-bipyrrolidine;
(3'S)-1'-[4-(4-methoxyphenoxy)benzoyl]-1,3'-bipyrrolidine;
(3'S)-1'-[4-(4-chloro-2-methylphenoxy)benzoyl]-1,3'-bipyrrolidine;
(3'S)-1'-[4-(2-chloro-4-methylphenoxy)benzoyl]-1,3'-bipyrrolidine;
(3'S)-1'-[4-(2-methylphenoxy)benzoyl]-1,3'-bipyrrolidine;
(3'S)-1'-{4-[4-(4-fluorophenoxy)phenoxy]benzoyl}-1,3'-bipyrrolidine;
(3'S)-1'-{4-[3-(3-fluorophenoxy)phenoxy]benzoyl}-1,3'-bipyrrolidine;
(3'S)-1'-{4-[(4-chloro-1-napthyl)oxy]benzoyl}-1,3'-bipyrrolidine;
a stereoisomer thereof; and
a pharmaceutically acceptable salt thereof.

* * * * *